United States Patent
Meier et al.

(10) Patent No.: US 8,895,533 B2
(45) Date of Patent: Nov. 25, 2014

(54) STARCH DERIVATIVE MIXTURES

(75) Inventors: Bernd Meier, Darmstadt (DE); Iris Theresia Jankowiak-Meier, Darmstadt (DE); Nele Meier, Darmstadt (DE); Clara Meier, Darmstadt (DE)

(73) Assignee: B. Braun Melsungen AG, Melsungen (DE)

( * ) Notice: Subject to any disclaimer, the term of this patent is extended or adjusted under 35 U.S.C. 154(b) by 0 days.

(21) Appl. No.: 13/513,943

(22) PCT Filed: Dec. 6, 2010

(86) PCT No.: PCT/EP2010/068950
§ 371 (c)(1),
(2), (4) Date: Aug. 21, 2012

(87) PCT Pub. No.: WO2011/067403
PCT Pub. Date: Jun. 9, 2011

(65) Prior Publication Data
US 2013/0005685 A1  Jan. 3, 2013

(30) Foreign Application Priority Data

Dec. 6, 2009 (DE) .......... 10 2009 056 832

(51) Int. Cl.
| | | |
|---|---|---|
| *A61K 31/718* | (2006.01) | |
| *A61K 31/715* | (2006.01) | |
| *C08B 31/00* | (2006.01) | |
| *C08B 31/02* | (2006.01) | |
| *C08B 31/08* | (2006.01) | |
| *A61K 9/00* | (2006.01) | |
| *A61K 45/06* | (2006.01) | |
| *C08L 3/06* | (2006.01) | |
| *C08L 3/08* | (2006.01) | |

(52) U.S. Cl.
CPC ............. *A61K 9/0026* (2013.01); *A61K 31/718* (2013.01); *A61K 45/06* (2013.01); *C08L 3/06* (2013.01); *C08L 3/08* (2013.01); *C08L 2205/02* (2013.01)
USPC .............. 514/60; 514/54; 536/102; 536/110; 536/107; 536/111

(58) Field of Classification Search
USPC ................ 514/60, 54; 536/102, 110, 107
See application file for complete search history.

(56) References Cited

FOREIGN PATENT DOCUMENTS

| | | |
|---|---|---|
| DE | 41 23 001 A1 | 1/1993 |
| EP | 1 190 719 A1 | 3/2002 |
| EP | 1 230 935 A2 | 8/2002 |
| EP | 1230935 A2 * | 8/2002 |
| EP | 1 473 308 A1 | 11/2004 |
| WO | WO 2005/082942 A2 | 9/2005 |

OTHER PUBLICATIONS

Maier et al.; EP 1230935 A2; Aug. 14, 2002 (English Machine Translation).*
International Search Report, Application No. PCT/EP2010/-68950; Sep. 6, 2011.

* cited by examiner

*Primary Examiner* — Layla Bland
*Assistant Examiner* — Michael C Henry
(74) *Attorney, Agent, or Firm* — RatnerPrestia

(57) ABSTRACT

The invention relates to a compound, comprising
a) a first starch derivative selected from the group consisting of hydroxyalkyl starch, carboxyl alkyl starch, ester starch and arbitrary mixtures thereof, wherein the starch derivative has a mean relative molar mass Mw1 and a degree of molar substitution MS1, and
b) a second starch derivative selected from the group consisting of hydroxyalkyl starch, carboxyl alkyl starch, ester starch and arbitrary mixtures thereof, having a mean relative molar mass Mw2 and a degree of molar substitution MS2, characterized in that Mw1 is greater than Mw2 (Mw1>Mw2) and MS2 is greater than MS1 (MS2>MS1).

17 Claims, No Drawings

STARCH DERIVATIVE MIXTURES

CROSS REFERENCE TO RELATED APPLICATIONS

This application is the U.S. national phase under 35 U.S.C. §371 of International Application No. PCT/EP2010/068950, filed Dec. 6, 2010, which claims priority to DE Application No. 102009056832.8, filed Dec. 6, 2009, the contents of each of which are Incorporated by reference in their entirety for all purposes.

FIELD OF THE INVENTION

The invention relates to compositions comprising a first starch derivative and a second starch derivative, wherein the average molecular weight of the first starch derivative is higher than the average molecular weight of the second starch derivative, and the molar substitution of the second starch derivative is higher than the molar substitution of the first starch derivative. Further, the invention relates to a pharmaceutical formulation comprising such a starch derivative composition, and to a process for preparing such a composition.

BACKGROUND OF THE RELATED ART

The dilemma of artificial plasma replacement solutions resides in the fact that the chemical modification of biopolymers provides stable colloids soluble in blood on the one hand, but leaves colloid molecules in the body, which are stored in the organs, on the other. The infusion of hydroxyalkyl starch and carboxyalkyl starch solutions serves for the replacement of blood or its plasma components. The infused colloids are supposed to maintain the physiological colloid-osmotic pressure, which is essentially attributed to albumin. The vapor pressure lowering caused by the dispersed colloids promotes the influx of water from the interstitial tissue into the blood vessels. This effect plays an essential role, in particular, in septic patients, in whom significant displacements of water from the blood into the interstitial tissue occurs because of barrier disorders between the interstitial tissue and the blood. Further effects include the positive effect of the water retained in the blood vessels on the flow properties of the blood, and the promotion of laminar flows within the vessels. Hydroxyalkyl starches are usually prepared from potato or waxy maize starch. Being naturally grown polymer compounds, they have molecular weights and branching patterns that are very different from molecule to molecule. After hydrolytic cleavage into smaller and more unitary molecules that are distributed relatively closely around a defined average of the molecular weight, a defined amount of hydroxyalkyl groups is introduced into the colloid for improving the water solubility and for protection from enzymatic cleavage. Such modified starch preparations are characterized by two quantities, the molar substitution, MS, and the average molecular weight, Mw. The molar substitution MS corresponds to the total number of hydroxyethyl groups per the total number of glucose molecules. The molecular weight Mw corresponds to the weight average of all molecules of the polydisperse colloid mixture. The narrow molecular weight distribution around the average molecular weight is considered a quality criterion for the hydroxyethyl starch solutions approved as medicaments. The elimination of hydroxyalkyl and carboxyalkyl starch is believed to be primarily dependent on the molar substitution MS. The influence of the molar substitution on the elimination rate for hydroxyethyl starch is based on the steric hindrance of the enzymatic attack by hydrolytically acting enzymes. The higher the number of hydroxyethyl groups introduced into the starch molecule, the more slowly is the hydroxyethyl starch excreted. The infusion of hydroxyalkyl starches is quantitatively limited because of its being stored in the RHS (reticulohistiocytic system) and the impairment resulting therefrom, which is discussed very controversially. Since highly substituted colloids, above all, are phagocytosed and stored to a higher extent, the molar substitution of more recent HES solutions is clearly reduced. The hydrolytic degradation of hydroxyethyl starch in blood is mainly explained by the activity of α-amylase. The enzyme, a tetramer having a molecular weight of about 60 kDa, cleaves off glucose residues, maltose or maltotrioses from the terminal portions of hydroxyethyl starch. The cleavage of the 1,6-branching sites and the hydrolytic separation of longer residues are less frequent, depending on the degree of branching of the starting starch. After infusion, the proportion of C2-substituted hydroxyalkyl glucoses as compared to C6-substituted ones is clearly increased. With hydroxyethyl starch infusions in healthy subjects, Weitler and Sommermeier and Förster et al. made the following observations:

The width of the molecular weight distribution of hydroxyethyl starch present in blood decreases with time after the infusion. In the urine, the average molecular weight significantly increases with time. After infusion of a hydroxyethyl starch (HES) (e.g., Mw: 200 kDa; MS: 0.5), the molecular weight of the HES excreted in the urine increases (from 20 kDa to 40 kDa). No molecular weights above 70 kDa were found in the urine of healthy subjects. The substitution of the HES secreted in the urine increases to a similar extent that the molar substitution of the hydroxyethyl starch remaining in the serum increases.

It is assumed that these molecules are stored by the cells of the RHS as so-called residual starches. Now, while the serum half life of an HES sufficiently correlates with its degree of substitution, which suggests the steric hindrance of hydrolytic enzymes, especially serum amylase, by the introduced hydroxyalkyl groups, the course of the secreted molecular weight sizes in the urine remains obscure.

The replacement of intravasal liquid belongs to the most important measures in the prophylaxis and therapy of hypovolemia, irrespective of whether the hypovolemia results from the direct loss of blood or body fluids (in acute bleeding, traumas, surgery, burns), from distribution disorders between the macro- and microcirculation (as in sepsis), or from a vasodilation (e.g., in the induction of anaesthesia). Infusion solutions suitable for these indications are to restore normovolemia and to maintain the perfusion of vital organs and the peripheral blood flow. At the same time, the solutions must not exceedingly stress the circulation, and they must be substantially free of side effects. In this respect, all the volume replacement solutions available to date offer both advantages and disadvantages. While so-called crystalloid solutions (electrolyte solutions) are substantially free from direct side effects, they ensure only a short-term or inadequate stabilization of the intravasal volume and hemodynamics. In pronounced or longer lasting hypovolemia, they must be infused in excessive amounts, because they do not remain exclusively in the intravasal compartment, but are quickly distributed in the extravasal space. However, a rapid drainage into the extravasal space not only limits the volume-replacing effect of crystalloid solutions, but also bears the risk of peripheral and pulmonary edemas. Apart from the vital threat that a pulmonary edema may mean, it additionally leads to a deterioration of nutritive oxygen supply, which is also adversely affected by peripheral edemas.

In contrast, colloidal volume replacement solutions have a far more reliable effect, irrespective of whether the colloids contained therein are of natural or synthetic origin. This is due to the fact that their colloid-osmotic effect causes them to longer retain the supplied liquid in the circulation as compared to crystalloids, thus protecting them from being drained into the interstitium. On the other hand, colloidal volume replacement solutions give rise to undesirable reactions to a higher extent as compared to crystalloid solutions. Thus, the natural colloid albumin, like all blood and plasma derivatives, bears the risk of infection with viral diseases; in addition, interactions with other drugs, such as ACE inhibitors, may occur; finally, the availability of albumin is limited, and its use as a volume replacement is disproportionately expensive. Further doubts as to the use of albumin as a volume replacement are due to the inhibition of the endogenous synthesis of albumin if it is added exogenously and due to its ready extravascularization. This means the passage from the circulation into the extravascular space, where undesirable and persistant liquid accumulations can occur because of the colloid-osmotic effect of albumin.

In the synthetic colloids, severe anaphylactoid responses and a massive inhibition of blood coagulation have caused dextran preparations to disappear almost completely from therapy. Although hydroxyethyl starch (HES) solutions also have the potential for triggering anaphylactoid responses and affecting blood coagulation, this is to a lesser extent as compared with dextran. Severe anaphylactoid responses (responses of severity III and IV) are observed extremely rarely with HES solutions, in contrast to dextran, and the influence on blood coagulation, inherent to the high-molecular weight HES solutions, could be significantly reduced in recent years by the further development of HES solutions. As compared with gelatin solutions, which also find use as plasma replacements and leave blood coagulation essentially unaffected, HES solutions, at least their high- and medium-molecular weight embodiments, have the benefit of a longer plasma residence time and effectiveness.

EP-A-0 402 724 discloses the preparation and use of a hydroxyethyl starch having an average molecular weight, Mw, of from 60,000 to 600,000, a molar substitution, MS, of from 0.15 to 0.5, and a degree of substitution, DS, of from 0.15 to 0.5. The disclosure deals with the rapid (6 to 12 hours) and complete degradability of the hydroxyethyl starches to be employed as plasma expanders. Within the preferred range of average molecular weights of from 100,000 to 300,000, a hydroxyethyl starch having an average molecular weight of 234,000 was explicitly examined.

U.S. Pat. No. 5,502,043 discloses the use of hydroxyethyl starches having an average molecular weight, Mw, of from 110,000 to 150,000, a molar substitution, MS, of from 0.38 to 0.5, and a degree of substitution, DS, of from 0.32 to 0.45 for improving microcirculation in peripheral arterial occlusive disease. In addition, the document teaches the use of low-molecular weight (Mw 110,000 to 150,000) hydroxyethyl starches which, due to their low molecular weight, keep the plasma viscosity low and thus ensure an improvement of microcirculation in the blood flow. However, this document advises against the use of higher-molecular weight hydroxyethyl starches, such as a hydroxyethyl starch with an Mw of 500,000, because they increase plasma viscosity and thus deteriorate microcirculation despite their low molar substitution (MS=0.28).

Worldwide, different HES preparations are currently used as colloidal volume replacements, which are mainly distinguished by their molecular weights and additionally by their extent of etherification with hydroxyethyl groups, and by other parameters. The best known representatives of this class of substances are the so-called Hetastarch (HES 450/0.7) and Pentastarch (HES 200/0.5). The latter is the currently most widespread "standard HES". Besides, HES 200/0.62 and HES 70/0.5 play a minor role. The declared information relating to the molecular weight as well as that relating to the other parameters are averaged quantities, where the molecular weight declaration is based on the weight average (Mw) expressed in daltons (e.g., for HES 200,000) or mostly abbreviated in kilodaltons (e.g., for HES 200). The extent of etherification with hydroxyethyl groups is characterized by the molar substitution MS (e.g. as 0.5 such as in HES 200/0.5; MS=average molar ratio of hydroxyethyl groups to anhydroglucose units) or by the degree of substitution (DS=ratio of mono- or polyhydroxyethylated glucoses to the total anhydroglucose units). According to their molecular weights, the HES solutions in clinical use are classified into high-molecular weight (450 kD), medium-molecular weight (200-250 kD) and low-molecular weight (70-130 kD) preparations.

As to the coagulation effects of HES solutions, a distinction is to be made between non-specific and specific influences. A non-specific influence on blood coagulation results from dilution of the blood (hemodilution), which occurs during the infusion of HES solutions and other volume replacements into the circulation. Affected by this hemodilution are also coagulation factors, whose concentrations are decreased depending on the extent and duration of the dilution of the blood and the plasma proteins due to the infusion. Correspondingly large or persisting effects may result in a hypocoagulability which is detectable by laboratory diagnostics and, in extreme cases, clinically relevant.

In addition, hydroxyethyl starch may cause a specific influence on blood coagulation, for which several factors are held responsible. Thus, under certain conditions or with certain HES preparations, a decrease of the coagulation proteins factor VIII (F VIII) and von Willebrand factor (vWF) is found which is larger than the general decrease of the plasma proteins due to hemodilution. Whether this larger than expected decrease is caused by a reduced formation or release of F VIII/vWF, such as by coating effects on the vascular endothelium caused by HES, or by other mechanisms is not quite clear.

However, HES influences not only the concentration of the coagulation factors mentioned but evidently also the function of platelets. This is completely or in part due to the binding of HES to the surface of the platelets, which inhibits the access of ligands to the fibrinogen receptor of the platelets.

These specific effects of HES on blood coagulation are particularly pronounced when high-molecular weight HES (e.g., HES 450/0.7) are employed while they do not play such a great role for medium-molecular weight (e.g., HES 250/0.5) or low-molecular weight HES (e.g., HES130/0.4 or HES 70/0.5) (J. Treib et al., Intensive Care Med. (1999), pp. 258 to 268; O. Langeron et al., Anesth. Analg. (2001), pp. 855 to 862; R. G. Strauss et al., Transfusion (1988), pp. 257-260; M. Jamnicki et al., Anesthesiology (2000), pp. 1231 to 1237).

If the risk profile of high-molecular weight HES is compared with that of the medium- and low-molecular weight preparations, a clear reduction of the risks can be established in the latter, i.e., not only with respect to the interaction with blood coagulation but also with respect to particular pharmacokinetic properties. Thus, the high-molecular weight HES solutions show a high accumulation in the circulation while this drawback is reduced in medium-molecular weight HES and virtually absent in low-molecular weight preparations. The fact that no more accumulation occurs with low-molecular weight HES solutions, such as HES130/0.4, is a relevant therapeutic progress because the plasma levels of HES cannot be determined in clinical routine, and therefore, even extreme concentrations, which can be obtained within a few days with the high-molecular weight solutions, remain undiscovered. In this case, the amount of "residual HES" accumulated in the circulation is unknown to the user but it nevertheless influences the kinetics and behavior of the HES which was additively infused, not knowing the amounts still present in the circulation. Therefore, the effect of high-molecular weight HES according to the prior art is not calculable; it remains longer in the circulation than would be required or desired for therapeutic reasons in most cases, and its metabolic fate is unclear.

In contrast, low-molecular weight HES will disappear completely from the circulation within about 20 to 24 hours after the infusion. This avoids backlog effects, and no accumulation occurs, especially for repeated infusions. The pharmacokinetic behavior of low-molecular weight starch, in contrast to high-molecular weight starch, is calculable and therefore can be easily controlled. Too high a load on the circulation or the clearance mechanisms does not occur.

However, this behavior of low-molecular weight HES as compared to high-molecular weight preparations, which is advantageous as such, is purchased at the expense of a significantly shorter plasma half life. The plasma half life of low-molecular weight HES is only about half that of HES 200 or less (3. Waitzinger et al., Clin. Drug Invest. (1998), pp. 151 to 160) and is in the range of the half life of gelatin preparations, which are to be rated as decidedly short-term effective. Although a short half life of a volume replacement need not be categorically disadvantageous, because it can be compensated for by a more frequent or more highly dosed administration of the volume replacement in question, in severe or persisting hypovolemia, a volume replacement with a short half life and short effective period involves the risk of insufficient circulation filling (much like with crystalloid solutions) or, when the dosage is correspondingly increased for compensating for this drawback, the risk of interstitial liquid overload.

Before this background, there is a need for a volume replacement which on the one hand is characterized by a low tendency to accumulation and a low influence on blood coagulation (such as low-molecular weight HES) but on the other hand has a longer half life as compared to the low-molecular weight HES solutions, whose properties are close to those of crystalloid solutions.

SUMMARY OF THE INVENTION

It has now been surprisingly found that compositions comprising at least two different starch derivatives will solve the problems mentioned in the prior art, and that, in particular, a longer plasma half life and at the same time a reduction of the remaining residual starch can be achieved.

Therefore, the invention relates to a composition comprising
a) a first starch derivative selected from the group consisting of hydroxyalkyl starch, carboxyalkyl starch, ester starch and any mixtures thereof, the starch derivative having an average molecular weight $Mw1$ and a molar substitution $MS1$; and
b) a second starch derivative selected from the group consisting of hydroxyalkyl starch, carboxyalkyl starch, ester starch and any mixtures thereof, with an average molecular weight $Mw2$ and a molar substitution $MS2$;

wherein $Mw1$ is greater than $Mw2$ ($Mw1>Mw2$), and $MS2$ is greater than $MS1$ ($MS2>MS1$).

DETAILED DESCRIPTION OF CERTAIN EMBODIMENTS OF THE INVENTION

The composition according to the invention is preferably optimized to minimum organ storage, wherein the first and second starch derivatives have sufficiently different average molecular weights and have such compositions that the starch derivatives having the higher molecular weight have a lower molar substitution, and the starch derivatives having the lower molecular weight have a higher molar substitution.

The molar substitution $MS1$ of the starch derivatives having the higher molecular weight is selected very low, so that cleavage into smaller molecular weight sizes is possible and storage in the organs is substantially omitted. Conversely, the second starch derivatives, which have lower average molecular weights, preferably sufficiently close to the kidney's molecular weight cut-off, have a higher molar substitution and accordingly have a high $MS2$ value.

In contrast to conventional hydroxyalkyl starch solutions, whose molecular weight fractions are hydroxyethylated together in one process, the compositions according to the invention are asymmetrically substituted. The molar substitution MS strongly decreases with higher molecular weights. Thus, the higher molar substitution provides smaller molecules with larger hydrodynamic radii as compared to the larger molecules in the solution.

In a preferred embodiment, the composition according to the invention comprises at least 2 starch derivatives, preferably hydroxyethyl starch and/or acetyl starch, wherein the second starch derivative having the lower average molecular weight has a significantly higher molar substitution as compared to the first starch derivative, and the first starch derivative (having the higher average molecular weight) has a significantly lower molar substitution. In an advantageous embodiment, an HES or an acetyl starch with an MW within a range of the kidney's molecular weight cut-off is so highly substituted that it is substantially protected from attack by the serum amylase, but still can be readily eliminated by the kidney considering its hydrodynamic radii, which are increased by the substitution. Conversely, the first starch derivative (having the higher molecular weight) has a much lower molar substitution. In another advantageous embodiment, the size distribution is adapted to the physiological conditions of human blood. For this purpose, the average molecular weight of the second starch derivative is on the order of that of albumin, and the average molecular weight of the second starch derivative is on the order of that of globulins.

The starch derivatives to be employed according to the invention are influenced by the molar substitution MS. The molar substitution MS is defined as the average number of hydroxyethyl groups per anhydroglucose unit (Sommermeyer et al., Krankenhauspharmazie (1987), pp. 271 to 278). The molar substitution can be determined according to Ying-Che Lee et al., Anal. Chem. (1983) 55, 334, and K. L. Hodges et al., Anal. Chem. (1979) 51, 2171. In this method, a known amount of HES is subjected to ether cleavage by adding adipic acid and hydroiodic acid (HI) in xylene. Subsequently, the ethyl iodide released is quantified by gas chromatography using an internal standard (toluene) and external standards (ethyl iodide calibrating solutions). The molar substitution MS influences the effect of the starch derivatives to be employed according to the invention.

Due to the preparation conditions, the starch derivatives to be employed according to the invention are not in the form of a substance with a defined uniform molecular weight but in the form of a mixture of molecules of different sizes which are also differently substituted by hydroxyethyl groups. Therefore, the characterization of such mixtures requires recourse to statistically averaged quantities. Therefore, the weight-average molecular weight (Mw) serves for characterizing the average molecular weight, the general definition of this mean value being stated in Sommermeyer et al., Krankenhauspharmazie (1987), pp. 271 to 278.

The molecular weight determination can be effected by means of GPC-MALLS using the GPC columns TSKgel G 6000 PW, G 5000 PW, G 3000 PW and G 2000 PW (7.5 mm×30 cm), the MALLS detector (DAWN-EOS; Wyatt Deutschland GmbH, Woldert) and the R1 detector (Optilab DSP; Wyatt Deutschland GmbH, Woldert) at a flow rate of 1.0 ml/minute in a 50 mM phosphate buffer, pH 7.0. The evaluation may be performed by means of ASTRA software (Wyatt Deutschland GmbH, Woldert).

Preferred are those starch derivatives which are obtainable from native or partially hydrolyzed cereal or potato starches. Waxy varieties of the corresponding crops, if they exist (e.g., waxy maize or waxy rice), are particularly preferred.

Surprisingly, it has been found that starch derivatives prepared from starches predominantly consisting of amylose are particularly useful in the present invention. Compositions according to the invention prepared from such starch derivatives are particularly suitable for aqueous infusions whose viscosity can be adjusted to an extraordinarily high extent by adding electrolytes.

In a particularly preferred embodiment, the starch derivatives to be employed according to the invention are based on starches having at least 50% by weight, preferably at least 65% by weight and especially at least 75% by weight, of amylose, the weight being based on the total weight of the starch.

The starch derivatives to be employed according to the invention can be further described by the ratio of substitution at $C_2$ to substitution at $C_6$ of the anhydroglucose units. This ratio, which is also abbreviated as $C_2/C_6$ ratio within the scope of this invention, means the ratio of the number of anhydroglucose units substituted in 2 position to the number of anhydroglucose units substituted in 6 position of the hydroxyethyl starch. The $C_2/C_6$ ratio of an HES can be varied widely by the amount of aqueous sodium hydroxide used in the hydroxyethylation, as shown in Tables 1 and 2. The higher the amount of NaOH employed, the more highly the hydroxy groups in 6 position in the anhydroglucose of the starch are activated for hydroxyethylation. Therefore, the $C_2/C_6$ ratio decreases during the hydroxyethylation with increasing NaOH concentration. The determination is effected as stated by Sommermeyer et al., Krankenhauspharmazie (1987), pp. 271 to 278. With increasing preference in the order given, the $C_2/C_6$ ratios are preferably from 3 to below 8, from 2 to 7, from 3 to 7, from 2.5 to smaller than or equal to 7, from 2.5 to 6, or from 4 to 6. Especially in the first starch derivative of the composition according to the invention, the $C_2/C_6$ ratio is another contribution to achieving the objects of the invention.

The composition according to the invention has at least two different starch derivatives that differ in both their average molecular weights and their molar substitutions. Therefore, the compositions usually have a bimodal or multimodal molecular weight distribution. Compositions in which the first starch derivative and/or the second starch derivative has as narrow as possible a molecular weight distribution curve are preferred.

According to the present invention, the first starch derivative is selected from the group consisting of hydroxyalkyl starch, carboxyalkyl starch, ester starch and any mixtures thereof, the starch derivative having an average molecular weight Mw1 and a molar substitution MS1. The average molecular weight Mw1 of the first starch derivative is higher than the average molecular weight Mw2 of the second starch derivative. On the other hand, however, the molar substitution MS1 of the first starch derivative is lower than the molar substitution MS2 of the second starch derivative. Thus, an optimum plasma residence time is achieved.

To the extent that the second starch derivative is excreted, which occurs predominantly renally, osmotically active molecules can be cleaved from the first starch derivative.

In a preferred embodiment, the first starch derivative has an average molecular weight of above 60,000 daltons, preferably from 100,000 to 850,000 daltons, especially from 150,000 to 650,000 daltons.

For achieving the object, it has been found advantageous if the molar substitution MS1 of the first starch derivative is below 0.35, preferably from 0.05 to 0.3, especially from 0.1 to 0.25.

In one embodiment of the present invention, the first starch derivative has an average molecular weight Mw1 of from 80 to 500 kDa and a molar substitution MS1 of below 0.5. In an advantageous embodiment, Mw1 is from 100 to 300 kDa, and MS1 is below 0.4. Even more advantageously, Mw1 is from 130 to 230 kDa, and MS1 is below 0.3.

According to the present invention, the second starch derivative is selected from the group consisting of hydroxyalkyl starch, carboxyalkyl starch, ester starch and any mixtures thereof, with an average molecular weight Mw2 and a molar substitution MS2.

The composition according to the invention preferably contains the second starch derivative with an average molecular weight Mw2 from 10,000 to 80,000 daltons, preferably from 10,000 to 60,000 daltons, more preferably from 30,000 to 80,000 daltons, especially from 40,000 to 70,000 daltons.

Preferably, the second starch derivative has a molar substitution MS2 of from 0.35 to 0.8, more preferably from 0.4 to 0.7, especially from 0.5 to 0.6.

In a preferred embodiment of the invention, the second starch derivative has an average molecular weight Mw2 that is below the kidney's molecular weight cut-off, and in particular, Mw2 is from 5 kDa to 60 kDa, and the molar substitution MS2 is from 0.5 to 0.9. In an advantageous embodiment, the second starch derivative has an average molecular weight Mw2 of from 10 to 45 kDa and a molar substitution MS2 of from 0.6 to 0.8; more advantageously, Mw2 is from 20 to 40 kDa, and MS2 is from 0.66 to 0.72.

For preferred compositions according to the invention, the first starch derivative and/or the second starch derivative is a hydroxyalkyl starch, especially hydroxyethyl starch.

More preferably, in the composition, the first starch derivative and/or the second starch derivative is a carboxyalkyl starch, preferably carboxymethyl starch and/or carboxyethyl starch.

Suitable compositions are preferably characterized in that the first starch derivative and/or the second starch derivative is an ester starch, especially a starch esterified with mono- or dicarboxylic acids, more particularly acetyl starch or propionyl starch.

Especially preferred compositions comprise a hydroxyethyl starch as the second starch derivative, and a hydroxyethyl starch or acetyl starch as the first starch derivative. Preferred compositions have a weight ratio of first starch derivative to second starch derivative of from 1:9 to 9:1, preferably from 1:5 to 8:1, more preferably from 1:3 to 4:1, especially from 1:1 to 3:1.

Preferably, the difference Mw1−Mw2 is at least 20,000 daltons, preferably at least 50,000 daltons, especially at least 100,000 daltons, for example, 150,000 daltons.

More preferably, the difference MS2−MS1 is at least 0.05, more preferably at least 0.1, particularly at least 0.15, and more particularly at least 0.2, for example, at least 0.3.

Preferred are mixtures in which the weight proportion of the first starch derivative is predominant. The compositions according to the invention preferably have a bimodal or even multimodal molecular weight distribution.

The present invention further relates to a pharmaceutical formulation containing the composition according to the invention.

In principle, the pharmaceutical formulation according to the invention can be provided in any possible galenic dosage form. In a preferred embodiment of the present invention, the pharmaceutical formulations according to the invention can be injected or infused intravenously. Therefore, the pharmaceutical formulations are preferably in the form of an aqueous solution or colloidal aqueous solution. Preferably, the formulations contain the composition according to the invention in a concentration of up to 20%, more preferably from 0.5 to 15%, more preferably from 2 to 12%, especially from 4 to 10%, for example, 6%.

Further preferred ranges are from 2 to 20%, more preferably from 4 to 15%, especially from 6 to 10%.

Unless stated otherwise, the amounts are expressed in %, which is to be understood as meaning g/100 ml of solution within the scope of the present invention.

The pharmaceutical formulations according to the invention in the form of colloid solutions provide an infusion suitable for being introduced in the human or animal body, which causes an advantageous controllable increase of the osmotic pressure (II) in the flowing blood while leaving a minimum proportion of highly substituted high molecular weight colloids in the body.

In a further embodiment, the pharmaceutical formulations according to the invention additionally contain sodium chloride, preferably from 0.6 to 2%, more preferably 0.9%. A 0.9% solution of sodium chloride in water is also referred to as "physiological saline". It has the same osmotic pressure as blood serum and is therefore suitable as an isotonic solution for intravenous injection or infusion. Any other osmotically effective substances may also be used for isotonization as long as they are physiologically safe and well tolerated, such as glucose, glucose substitutes (fructose, sorbitol, xylitol) or glycerol. Further, the formulations may contain one or more components selected from the group consisting of calcium chloride, calcium acetate, $C_2$- to $C_{10}$-monoalkanoic acids or polycarboxylic acids (for example, propionic acid, butanoic acid, dicarboxylic acids, oxalic acid, malonic acid, succinic acid, citric acid, glutaric acid, adipic acid), amino acids (for example, glycine, alanine, proline, leucine, isoleucine, histidine), acetoacetic acid, 3-hydroxybutyrate, 3-oxobutanoic acid, acetoacetate, and urea.

In another preferred embodiment, the pharmaceutical formulations may additionally contain further plasma-adapted electrolytes. The preparation of such isotonic formulations is known to the skilled person. An example of an isotonic solution with plasma-adapted electrolytes is the so-called Tyrode solution. It contains 0.8 g of NaCl, 0.02 g of KCl, 0.02 g of $CaCl_2$, 0.01 g of $MgCl_2$, 0.005 g of $NaH_2PO_4$, 0.1 g of $NaHCO_3$ and 0.1 g of glucose in 100 ml of distilled water. Another example is the so-called Ringer solution which contains 0.8% sodium chloride, 0.02% potassium chloride, 0.02% calcium chloride and 0.1% sodium hydrogencarbonate. Of course, the anions of the electrolytes may also be replaced by metabolizable anions; thus, for example, the sodium hydrogencarbonate in the Ringer solution may be replaced by 0.3 or 0.6% sodium lactate. A corresponding electrolyte composition or solution is known to the skilled person as "Ringer lactate". Further metabolizable anions which may be used alone or in combination are acetate (e.g., "Ringer acetate") or malate.

In another embodiment of the invention, the pharmaceutical formulations may also be in the form of hypertonic solutions. Hypertonic solutions are those having a higher osmotic pressure than that of the human blood. The application of hypertonic pharmaceutical formulations may be advantageous in certain clinical pictures. The required high osmotic pressures of hypertonic solutions is adjusted by adding corresponding amounts of osmotically effective substances, e.g., by sodium chloride, which may be used in concentrations of up to 7.5% and more for this purpose.

Just in the interplay with electrolytes, the pharmaceutical formulations according to the invention in the form of aqueous formulations, for example, infusions, show significant advantages over the HES-based formulations of the prior art. Namely, it has been surprisingly found that the formulations according to the invention can be controlled substantially more effectively in their viscosity behavior by adding electrolytes. This can also be utilized, for example, for diagnostic purposes after the formulation has been infused.

To avoid and reduce the risk of infections, the pharmaceutical formulations according to the invention are preferably subjected to sterile filtration or heat sterilization. Particularly suitable for the sterile filtration of aqueous or colloidal aqueous pharmaceutical formulations according to the invention are fine-pore filter cartridges, such as those provided by the company Sartorius under the trade name SARTPORE. Such filter cartridges with a pore diameter of 0.2 μm are suitable, for example. In addition, the pharmaceutical formulations according to the invention may be subjected to heat sterilization without the hydroxyethyl starches being adversely affected. Preferably, the heat sterilization is performed at a temperature above 100° C., more preferably from 105 to 150° C., especially from 110 to 130° C., for example, 121° C., for a period of up to 30 minutes, preferably up to 25 minutes, especially from 18 to 22 minutes.

In a preferred embodiment, the pharmaceutical formulation is a volume replacement. Volume replacements are used for replacing intravascular fluid in animal and human organisms. Volume replacements are used, in particular, in the prophylaxis and therapy of hypovolemia. It is not critical whether the hypovolemia results from the immediate loss of blood or body fluids, such as in acute bleeding, traumas, surgery, burns etc., or from disturbed distributions between macro- and microcirculation, such as in sepsis, or from vasodilation, such as during the initiation of anesthesia. The volume replacements are further classified into the so-called plasma replacements and the so-called plasma expanders. For the plasma replacements, the intravascularly applied volume of the agent also corresponds to the volume supplied to the vessels. In contrast, for the plasma expanders, the intravascularly applied liquid volume of the expander is lower than the volume actually supplied to the vessels. This phenomenon is based on the fact that the use of plasma expanders disturbs the oncotic equilibrium between the intra- and extravascular spaces and additional liquid volume flows from the extravascular space into the vascular system to be treated.

Plasma expanders are distinguished from plasma replacements essentially by the fact that the concentration of the hydroxyethyl starches according to the invention contained therein is increased and/or the concentration of the respective electrolytes causes an oncotic and/or osmotic imbalance.

The pharmaceutical formulation according to the invention may further contain a pharmaceutically active ingredient or combinations of active ingredients and thus serve as a medium for administering the active ingredients dissolved therein, especially by injection and infusion.

The present invention further relates to the use of a pharmaceutical formulation according to the invention for the preparation of a volume replacement or plasma replacement or plasma expander.

More preferably, the pharmaceutical formulations according to the invention may be used as a volume replacement or plasma replacement or plasma expander. Preferably, the pharmaceutical formulations serve for maintaining normovolemia. The maintaining of normovolemia is of particular importance for hemodynamic stability, which has a critical influence on the human or animal organism, for example, with respect to the blood pressure, the diuresis rate or the heart rate. In order to compensate a loss of intravascular liquid as quickly as possible and restore normovolemia, the pharmaceutical formulations according to the invention have proven particularly advantageous, because as compared to the plasma replacements known in the prior art, especially low-molecular weight HES solutions, such as HES130/0.4, they have an extended plasma half life, especially in the critical phase immediately after infusion. The plasma viscosity can be controlled and regulated very well by means of the pharmaceutical formulation according to the invention, and the fact that surprisingly it is not increased also provides for an improvement of microcirculation and for an improved nutritive oxygen supply to the tissues.

The invention further relates to the use of the pharmaceutical formulation according to the invention for maintaining normovolemia and/or for improving the macro- and microcirculation and/or for improving the nutritive oxygen supply and/or for stabilizing hemodynamics and/or for improving the volume efficiency and/or for reducing the plasma viscosity and/or for increasing anemia tolerance and/or for hemodilution, especially for therapeutic hemodilution in disturbed blood supply and arterial, especially peripheral arterial, occlusive diseases.

The pharmaceutical formulations according to the invention or the composition according to the invention are preferably used for the preparation of medicaments, especially medicaments for maintaining normovolemia and/or for improving the macro- and microcirculation and/or for improving the nutritive oxygen supply and/or for stabilizing hemodynamics and/or for improving the volume efficiency and/or for reducing the plasma viscosity and/or for increasing anemia tolerance and/or for hemodilution, especially for therapeutic hemodilution in disturbed blood supply and arterial, especially peripheral arterial, occlusive diseases.

In addition, the pharmaceutical formulations according to the invention or the compositions according to the invention are advantageously employed in methods for treating the maintenance of normovolemia and/or for improving the macro- and microcirculation and/or for improving the nutritive oxygen supply and/or for stabilizing hemodynamics and/or for improving the volume efficiency and/or for reducing the plasma viscosity and/or for increasing anemia tolerance and/or for hemodilution, especially for therapeutic hemodilution in disturbed blood supply and arterial, especially peripheral arterial, occlusive diseases.

Because of their influence on the magnesium balance, the compositions or pharmaceutical formulations according to the invention are also suitable for medicaments and diagnostic agents.

The invention further relates to the pharmaceutical formulation according to the invention for use in the prophylaxis or therapy of diseases selected from the group consisting of diseases with reduced colloid-osmotic pressure, posthemorrhagic anemia, shock, SIRS/sepsis, thrombolysis, apoplexy, and eclampsia.

The invention further relates to the use of the formulation according to the invention for treating dehydration, liquid and electrolyte deficiencies, protein deficiency. Further, the composition can be used as a replacement of blood components, carrier solution for medicaments, means for improving the thermodynamic quality of blood plasma/or blood serum, means for altering the refractive index increment of blood, nutritive solution, rheological agent, agent for improving the blood supply to organs, thrombosis prophylaxis, adjuvant for thrombolysis, venotonic agent, agent for improving the effectiveness of antiarrhythmic agents, and agent for administering magnesium.

The invention further relates to a process for the preparation of a composition according to the invention, comprising the following steps:
  a) providing a first starch derivative selected from the group consisting of hydroxyalkyl starch, carboxyalkyl starch, ester starch and any mixtures thereof, the starch derivative having an average molecular weight Mw1 and a molar substitution MS1;
  b) providing a second starch derivative selected from the group consisting of hydroxyalkyl starch, carboxyalkyl starch, ester starch and any mixtures thereof, with an average molecular weight Mw2 and a molar substitution MS2, wherein Mw1 is greater than Mw2 (Mw1>Mw2), and MS2 is greater than MS1 (MS2>MS1); and
  c) mixing said first starch derivative with said second starch derivative.

It has surprisingly been found that starch derivatives having a low molecular weight can be prepared from high molecular weight starch derivatives by ultrasonic degradation. Therefore, it is preferred for the second starch derivative to be obtainable by ultrasonic degradation.

In a preferred embodiment, the composition according to the invention can be obtained by the delayed addition of starch molecules with increasing molecular weight during the process of chemical introduction of the substituent (hydroxyethylation, carboxymethylation, acetylation). Thus, colloids with higher molecular weights are provided with correspondingly lower molar substitutions.

EXAMPLE 1

By the process described by De Belder and Granath (Carbohydrate Research 30 (1973), 375-378), fluorescence-labeled hydroxyethyl starch (FITC-HES) having an average molecular weight Mw of 40 kDa and a molar substitution MS of 0.5 is prepared.

A.: 4 ml of an aqueous 6% FITC-HES 40,000/0.5 is mixed with 6 ml of an aqueous NaCl solution (0.9%). The solution is infused to three Wistar rats through a central venous catheter.

B.: 4 ml of the 6% FITC-HES 40,000/0.5 and 6 ml of an aqueous (10%) acetyl starch solution (200,000 daltons; MS 0.3) are also infused to three Wistar rats through a central venous catheter.

In both groups, the urine of the first hour is collected and examined with a fluorescence detector. It is found that 60 minutes after the infusion, the fluorescence measured in the urine (585 nm) in the animals having obtained 4 ml of 6% FITC-HES 40,000/0.5+6 ml of acetyl starch (200,000; MS 0.3) was 15-20% below the fluorescence excretion of the animals having obtained 4 ml of 6% FITC-HES 40,000/0.5+6 ml of NaCl 0.9%. After both infusions, comparable fluorescence captures were measured in circulating blood cells using flow cytometry.

EXAMPLE 2

A mixture of hydroxyethyl starches (1) containing 33.3 percent by weight of a hydroxyethyl starch (Mw: 40 kDa; MS=0.55) is mixed with 66.6 percent by weight of a hydroxyethyl starch (Mw: 130 kDa; MS=0.4).

A: Dispersions of this mixture of hydroxyethyl starches (1) having different concentrations in a saline (0.9% NaCl solution containing 154 mmol/l $Na^+$ and 154 mmol/l $Cl^-$) were prepared with the following concentrations: 2% (2 g/100 ml), 4% (4 g/100 ml), 6% (6 g/100 ml), 8% (8 g/100 ml), and 10% (10 g/100 ml).

B: Dispersions of this mixture of hydroxyethyl starches (1) having different concentrations in a saline that additionally contains magnesium acetate (6 mmol/l magnesium acetate tetrahydrate; NaCl solution containing 136 mmol/l $Na^+$ and 136 mmol/l $Cl^-$) were prepared with the following concentrations: 2% (2 g/100 ml), 4% (4 g/100 ml), 6% (6 g/100 ml), 8% (8 g/100 ml), and 10% (10 g/100 ml).

The 6% solution has an osmotic pressure of 53-58 mm Hg as measured with a 10 kDa membrane.

The viscosities of the colloid dispersions prepared under A and B are measured with different shear rates using a HAAKE MARS Rheometer at 310° K and with a gap width of 0.052 mm.

2.1 Examination of the Formulations Having a Concentration of 2% at Different Shear Rates.

At a lower shear rate of 56.4/s, a viscosity of 1.11 mPas was measured for the 2% solution A, and a viscosity of 1.44 mPas was measured for the corresponding 2% solution B.

At higher shear rates of 117/s, solution A shows a viscosity of 1.07 mPas, and solution B shows a viscosity of 1.15 mPas.

At a shear rate of 500/s, both solutions show the same viscosity, namely 1.01 mPas for A, and 1.01 mPas for B.

2.2 Examination of the Formulations Having a Concentration of 4% at Different Shear Rates.

Also for the 4% dispersions, larger differences between dispersion A and dispersion B were found at lower shear rates: At a shear rate of 56.4/s, a viscosity of 1.47 mPas was measured for dispersion A, and a viscosity of 1.75 mPas was measured for B.

At 500/s, A showed a viscosity of 1.34 mPas, and B showed a viscosity of 1.36 mPas.

2.3 Examination of the Formulations Having a Concentration of 8% at Different Shear Rates.

At a concentration of 8%, the following viscosity values were measured:

Shear rate: 56.4/s. Dispersion A shows a viscosity of 2.35 mPas, dispersion B of 2.60 mPas.

Shear rate: 117/s. Dispersion A shows a viscosity of 2.38 mPas, dispersion B of 2.42 mPas.

Shear rate: 500/s. Dispersion A shows a viscosity of 2.41 mPas, dispersion B of 2.43 mPas.

2.4 Examination of the Formulations Having a Concentration of 10% at Different Shear rates.

At a concentration of 10%, the following viscosity values were measured:

Shear rate: 56.4/s. Dispersion A shows a viscosity of 2.78 mPas, dispersion B of 2.97 mPas.

Shear rate: 117/s. Dispersion A shows a viscosity of 2.79 mPas, dispersion B of 2.94 mPas.

Shear rate: 500/s. Dispersion A shows a viscosity of 2.81 mPas, dispersion B of 2.97 mPas.

At 10% concentrations, the viscosities of dispersion B remained constantly and significantly above the values of dispersions A.

The results demonstrate the surprisingly high influence of the electrolytes on the viscosity behavior. Especially when magnesium-containing electrolytes are used, the viscosity of the colloidal infusions can be readily controlled.

The invention claimed is:

1. A pharmaceutical formulation comprising
    a) a composition comprising
        i) a first starch derivative selected from the group consisting of hydroxyalkyl starch, carboxyalkyl starch, ester starch and any mixtures thereof, the first starch derivative having an average molecular weight Mw1 and a molar substitution MS1; and
        ii) a second starch derivative selected from the group consisting of hydroxyalkyl starch, carboxyalkyl starch, ester starch and any mixtures thereof, with an average molecular weight Mw2 and a molar substitution MS2;
        wherein Mw1 is greater than Mw2 (Mw1>Mw2), and MS2 is greater than MS1 (MS2>MS1), wherein the weight ratio of the first starch derivative to the second starch derivative is from 1:9 to 9:1, and wherein the second starch derivative has an average molecular weight Mw2 from 30,000 to 80,000 daltons; and
    b) one or more electrolytes selected from the group consisting of sodium chloride, potassium chloride, magnesium acetate and magnesium chloride.

2. The pharmaceutical formulation according to claim 1, wherein said second starch derivative has a molar substitution MS2 of from 0.35 to 0.8.

3. The pharmaceutical formulation according to claim 1, wherein said first starch derivative has an average molecular weight of above 60,000 daltons.

4. The pharmaceutical formulation according to claim 1, wherein the molar substitution MS1 of the first starch derivative is below 0.35.

5. The pharmaceutical formulation according to claim 1, wherein said first starch derivative and/or said second starch derivative is a hydroxyalkyl starch.

6. The pharmaceutical formulation according to claim 1, wherein said first starch derivative and/or said second starch derivative is a carboxyalkyl starch.

7. The pharmaceutical formulation according to claim 1, wherein said first starch derivative and/or said second starch derivative is an ester starch.

8. The pharmaceutical formulation according to claim 1, wherein said first starch derivative and/or said second starch derivative is based on at least 50% by wei ht of amylose.

9. The pharmaceutical formulation according to claim 1, wherein the pharmaceutical formulation is in the form of an aqueous solution or colloidal aqueous solution.

10. The pharmaceutical formulation according to claim 1, wherein the formulation is aqueous, and said composition comprising said first starch derivative and said second starch derivative is present in an amount of from 2 to 20% by weight.

11. The pharmaceutical formulation according to claim 1, wherein one or more components selected from the group consisting of calcium chloride, calcium acetate, $C_2$- to $C_{10}$-monoalkanoic acids and polycarboxylic acids, amino acids, acetoacetic acid, p-hydroxybutyrate, 3-oxobutanoic acid, acetoacetate, and urea are present.

12. The pharmaceutical formulation according to claim 1, wherein the formulation is isotonic.

13. The pharmaceutical formulation according to claim 1, wherein the pharmaceutical formulation is a volume replacement.

14. The pharmaceutical formulation according to claim 1, containing a pharmaceutically active substance or a combination of pharmaceutically active substances.

15. A plasma replacement or plasma expander comprising the pharmaceutical formulation according to claim 1.

16. A process for the preparation of a pharmaceutical formulation, comprising the following steps:
   a) providing a first starch derivative selected from the group consisting of hydroxyalkyl starch, carboxyalkyl starch, ester starch and any mixtures thereof, the first starch derivative having an average molecular weight $Mw1$ and a molar substitution $MS1$;
   b) providing a second starch derivative selected from the group consisting of hydroxyalkyl starch, carboxyalkyl starch, ester starch and any mixtures thereof, with an average molecular weight $Mw2$ and a molar substitution $MS2$, wherein $Mw1$ is greater than $Mw2$ ($Mw1>Mw2$), and $MS2$ is greater than $MS1$ ($MS2>MS1$);
   c) providing one or more electrolytes selected from the group consisting of sodium chloride, potassium chloride, magnesium acetate and magnesium chloride; and
   d) mixing said first starch derivative with said second starch derivative and said one or more electrolytes, wherein the first starch derivative and the second starch derivative are present in the pharmaceutical formulation in a weight ratio of from 1:9 to 9:1 and wherein the second starch derivative has an average molecular weight $Mw2$ from 30,000 to 80,000 daltons.

17. The process according to claim 16, wherein said second starch derivative is obtained by ultrasonic degradation.

\* \* \* \* \*